US012708410B2

(12) United States Patent
Daniels

(10) Patent No.: US 12,708,410 B2
(45) Date of Patent: Aug. 18, 2026

(54) ROD REDUCTION DEVICE

(71) Applicant: OrthoPediatrics Corporation, Warsaw, IN (US)

(72) Inventor: David Wayne Daniels, Winona Lake, IN (US)

(73) Assignee: OrthoPediatrics Corp., Warsaw, IN (US)

( * ) Notice: Subject to any disclaimer, the term of this patent is extended or adjusted under 35 U.S.C. 154(b) by 354 days.

(21) Appl. No.: 18/025,587

(22) PCT Filed: Sep. 8, 2021

(86) PCT No.: PCT/US2021/049503

§ 371 (c)(1),
(2) Date: Mar. 9, 2023

(87) PCT Pub. No.: WO2022/056025

PCT Pub. Date: Mar. 17, 2022

(65) Prior Publication Data

US 2024/0008905 A1 Jan. 11, 2024

Related U.S. Application Data

(60) Provisional application No. 63/076,332, filed on Sep. 9, 2020.

(51) Int. Cl.
*A61B 17/70* (2006.01)

(52) U.S. Cl.
CPC ................................ *A61B 17/7086* (2013.01)

(58) Field of Classification Search
CPC ............ A61B 17/7086; A61B 17/7083; A61B 17/708; A61B 17/7088; A61B 17/7089
See application file for complete search history.

(56) References Cited

U.S. PATENT DOCUMENTS

2014/0277170 A1* 9/2014 Barrett ............... A61B 17/7085 606/279
2019/0069934 A1* 3/2019 Mickiewicz ......... A61B 17/708
2021/0015525 A1* 1/2021 Park ................... A61B 17/7086

* cited by examiner

*Primary Examiner* — Julianna N Harvey
(74) *Attorney, Agent, or Firm* — FBT Gibbons LLP

(57) ABSTRACT

A rod reduction device includes a body having a housing defining a cavity; a first member and a second member; a first finger assembly and a second finger assembly being secured to respective distal ends of the first member and the second member and configured to releasably engage a vertebral anchor therebetween; and a screw assembly defining a longitudinal axis, at least a portion of the screw assembly being positioned within the cavity of the housing. The screw assembly includes an inner shaft having exterior threading; and an outer shaft circumscribing the inner shaft and having interior threading threadably engaged with the exterior threading of the inner shaft. At least a portion of the outer shaft is rotatably coupled to the housing. The inner shaft is movable along the longitudinal axis upon rotation of the outer shaft and configured to reduce a spinal rod into the vertebral anchor.

15 Claims, 10 Drawing Sheets

ROD REDUCTION DEVICE

REFERENCE TO RELATED APPLICATION

This application claims priority to U.S. Provisional Application No. 63/076,332, filed Sep. 9, 2020, and which is incorporated herein by reference in its entirety.

TECHNICAL FIELD

The present disclosure relates to a device for use in spinal surgery. Spinal implants, including connectors, hooks, screws and rods, are used to correct spinal deformities. Screws and connectors in combination with spinal rods can align and correct deformities in the natural spinal alignment as well as repair traumatic injury. Instrumentation for the reduction of spinal rods into spinal pedicle screws is provided in the present disclosure.

BACKGROUND

Spinal fixation systems may be used in surgery to fix, adjust, and/or align the spinal column. One type of spinal fixation system employs a spinal rod for supporting the spine and fixing, adjusting, and/or aligning the spinal column into the desired orientation. Attachment of the spinal rod to the spinal column has been achieved using a variety of vertebral anchors. Vertebral anchors include screws, hooks, pins, and bolts used to engage the vertebrae and connect the spinal rod to different vertebrae.

The spinal rods in a spinal fixation system may necessarily be bent to conform to a desired curvature of the spinal column in one or more of the anatomic planes as part of a spinal fixation or corrective surgery. Attachment of spinal rods to the vertebral anchors may be complicated by differing curvature of the untreated spine and the curvature of the spinal rod. Instrumentation to force the spinal rod into engagement with the vertebral anchors may be used. Challenges arise in utilizing instrumentation to force the spinal rod into engagement with the vertebral anchors because the instrumentation generally must be releasably affixed to a previously implanted vertebral anchor and the locking mechanism on the vertebral anchor must be engaged while maintaining the spinal rod in the correct position. Simple engagement of the instrumentation with the vertebral anchor is desirable.

SUMMARY

Accordingly, an exemplary embodiment provides a rod reduction device comprising a body including a housing defining a cavity; a first member and a second member, each of the first and second members extending distally from the housing; a first finger assembly and a second finger assembly being secured to respective distal ends of the first member and the second member, wherein the first finger assembly and the second finger assembly are configured to, collectively, releasably engage a vertebral anchor therebetween; and a screw assembly defining a longitudinal axis, at least a portion of the screw assembly being positioned within the cavity of the housing. The screw assembly comprises an inner shaft having exterior threading; and an outer shaft having interior threading and circumscribing the inner shaft. At least a portion of the outer shaft is rotatably coupled to the housing. The exterior threading of the inner shaft is threadably engaged with the interior threading of the outer shaft. The inner shaft is movable along the longitudinal axis upon rotation of the outer shaft and configured to reduce a spinal rod into the vertebral anchor.

BRIEF DESCRIPTION OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
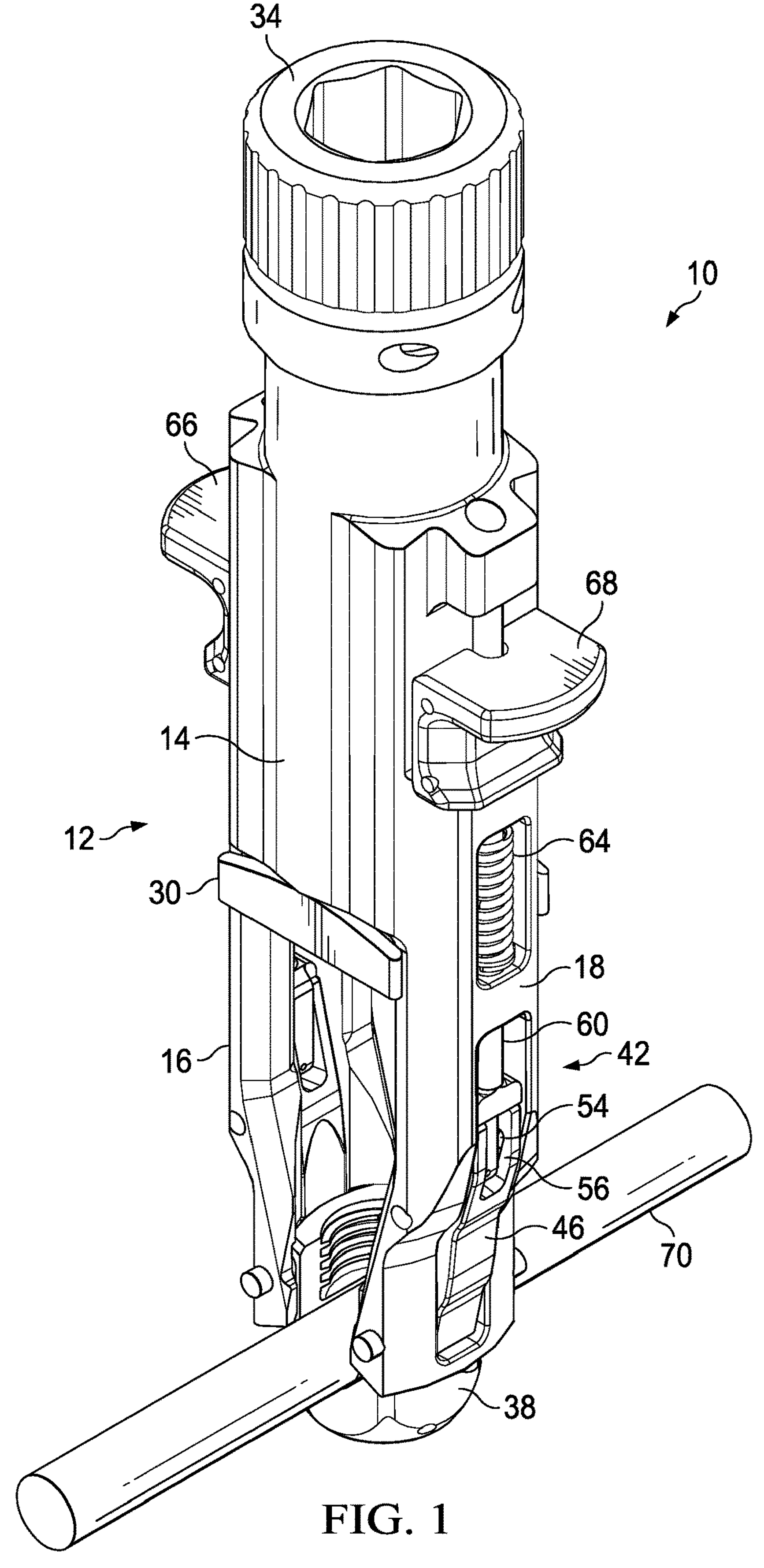
FIG. 1 is an isometric view of an embodiment of a rod reduction device in a retracted position.
Figure 2:
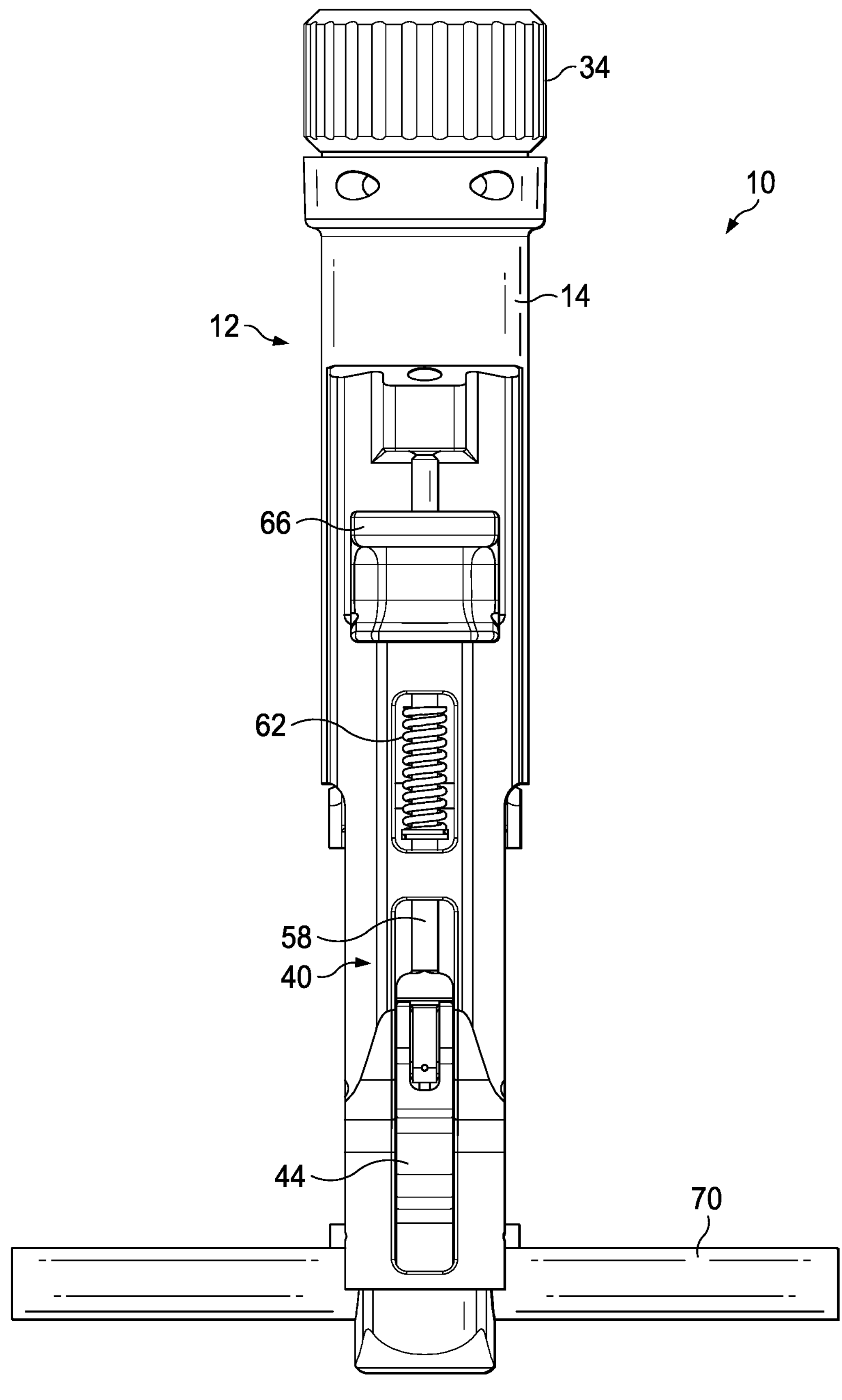
FIG. 2 is a side view of the rod reduction device of FIG. 1 in the retracted position.
Figure 3:
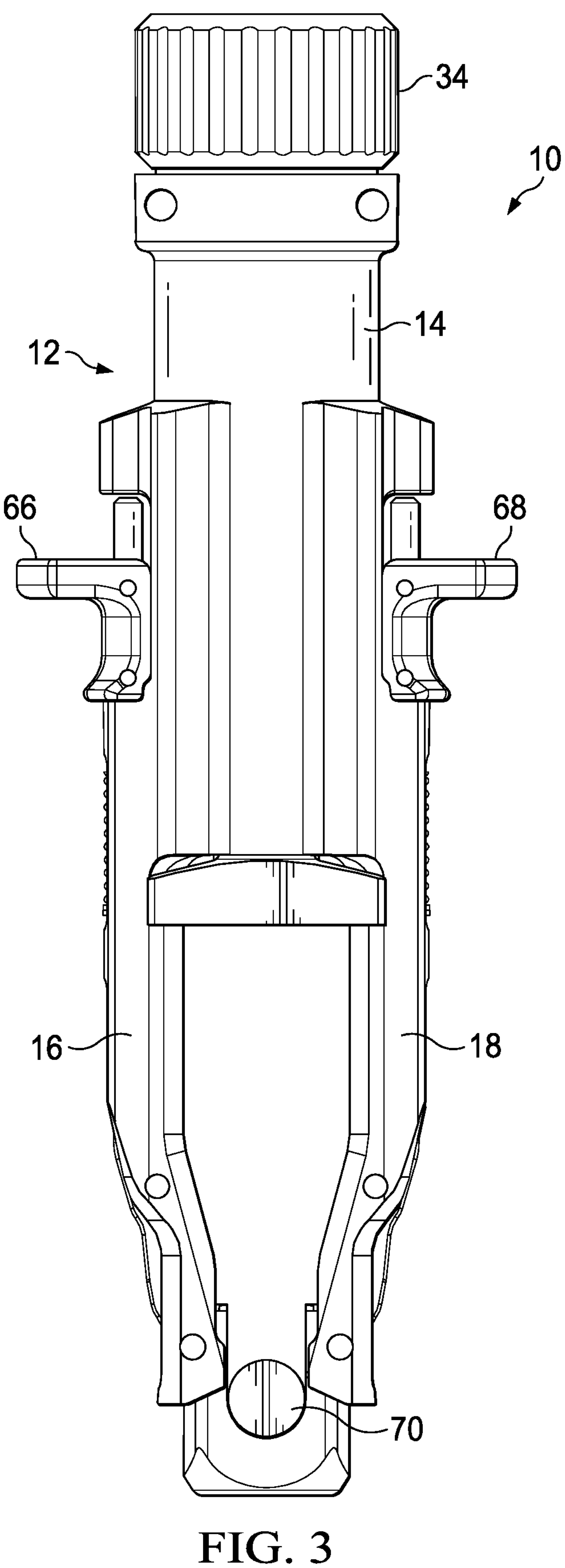
FIG. 3 is a front view of the rod reduction device of FIG. 1 in the retracted position.

Referring initially to FIGS. 1-4, an isometric view of a rod reduction device 10 is shown. The rod reduction device 10 can include a body 12 having a housing 14. The device 10 can further include a first member 16 and a second member 18, both of which can extend distally from the housing 14 and define a channel 20 therebetween. The housing 14 can define a cavity 22 configured to receive a screw assembly 24. The screw assembly 24 can define a longitudinal axis and extend through the cavity 22, along the longitudinal axis that is coincident between each of the cavity 22 and the screw assembly 24, such that a portion of the screw assembly 24 can further extend into the channel 20.

Figure 4:
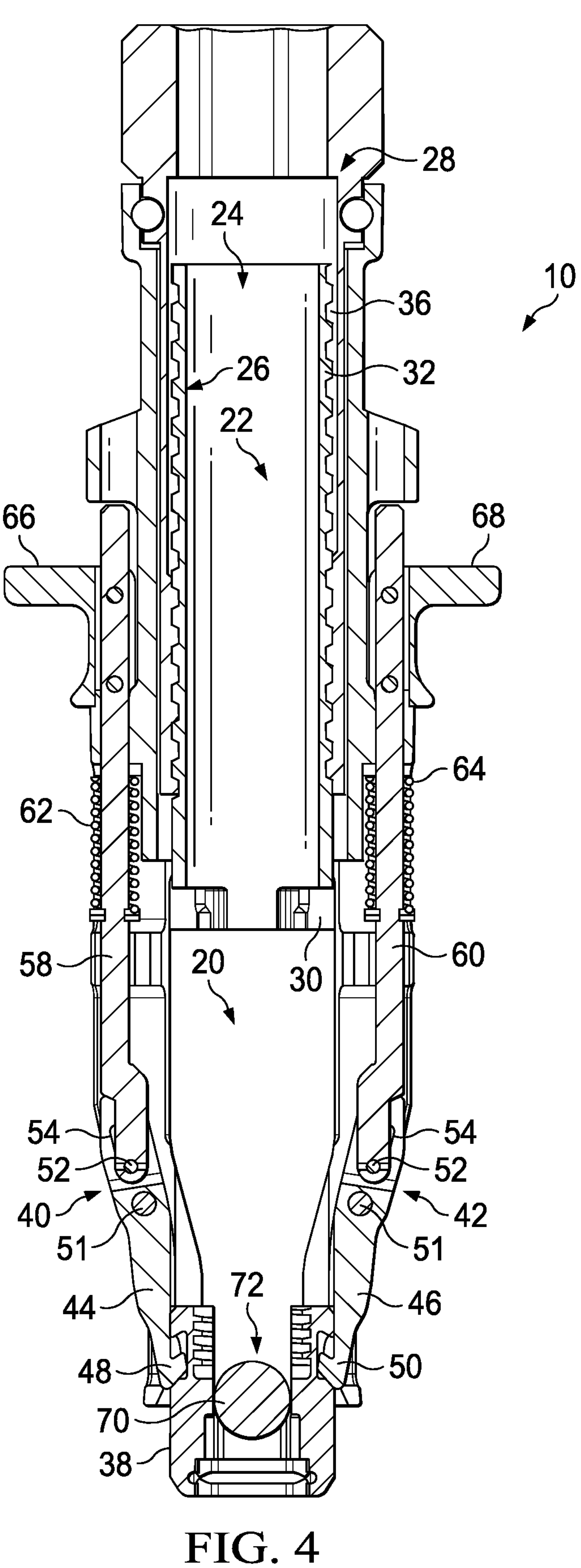
FIG. 4 is a cross-sectional view of the rod reduction device of FIG. 1 in the retracted position.
Figure 5:
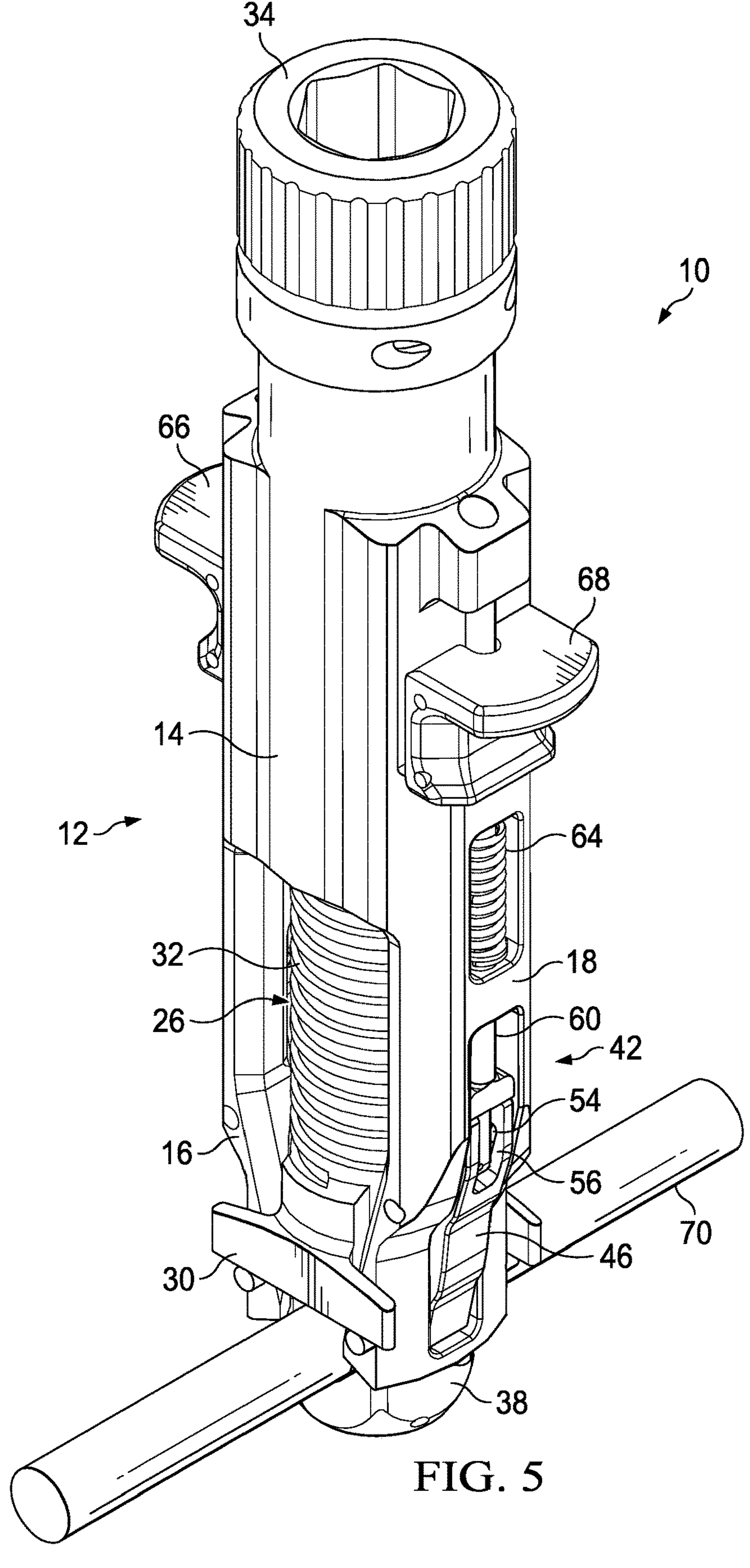
FIG. 5 is an isometric view of an embodiment of a rod reduction device in a reduced position.
Figure 6:
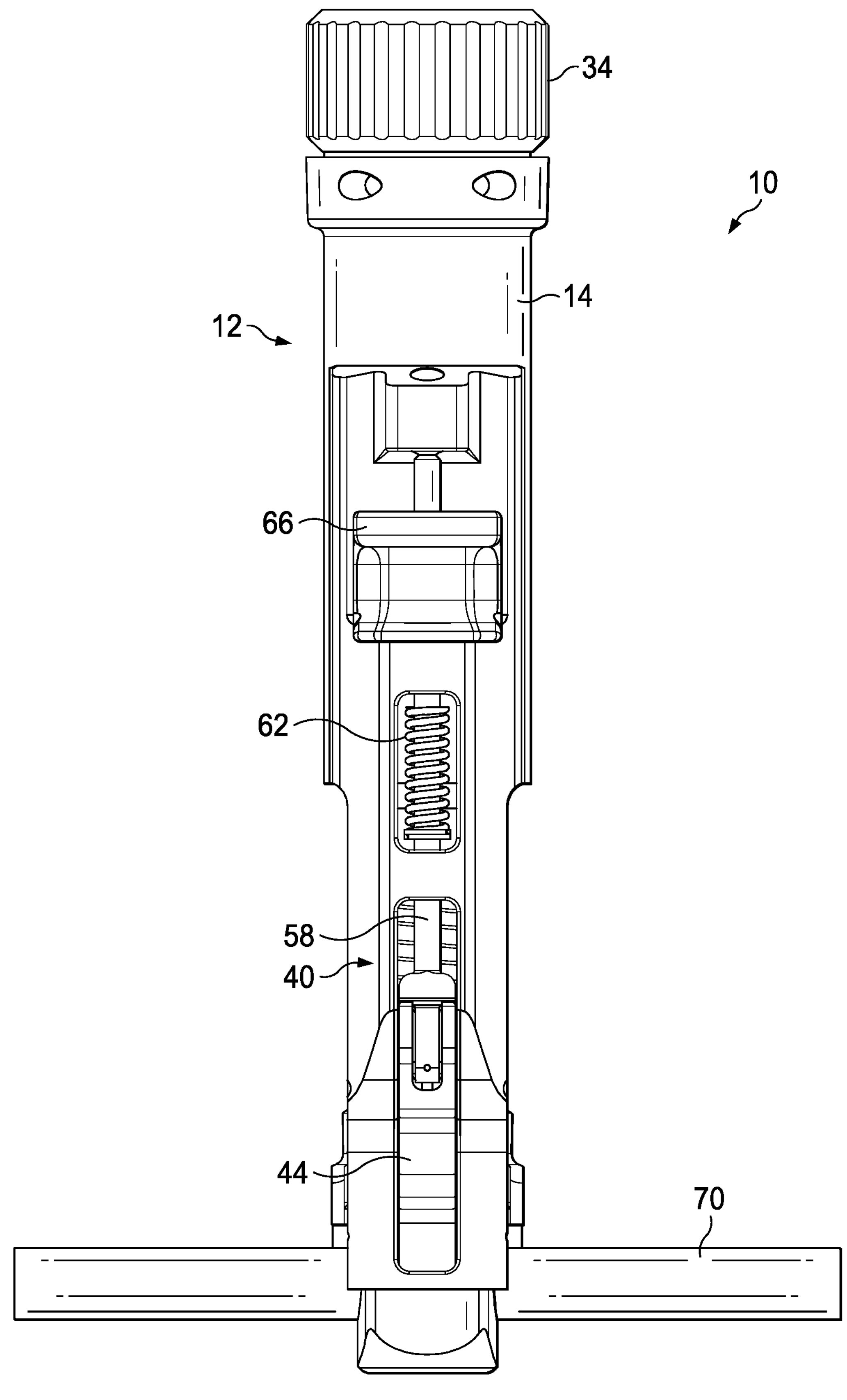
FIG. 6 is a side view of the rod reduction device of FIG. 1 in the reduced position.
Figure 7:
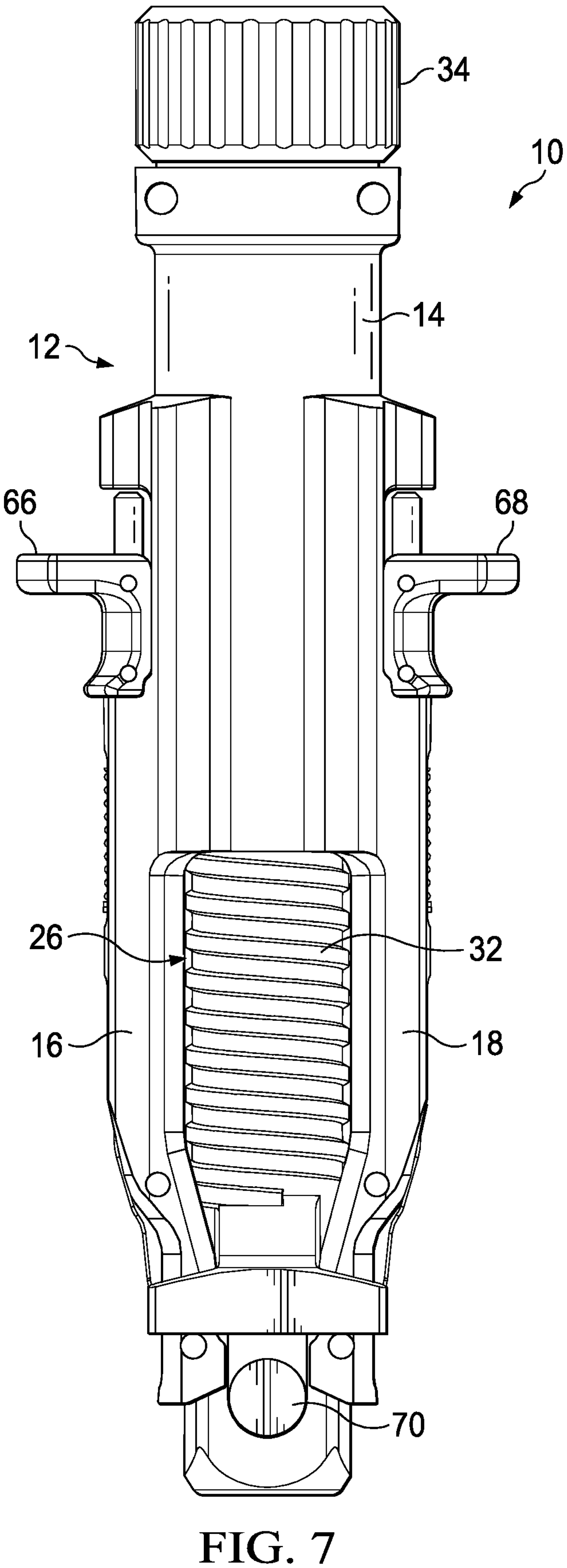
FIG. 7 is a front view of the rod reduction device of FIG. 1 in the reduced position.
Figure 8:
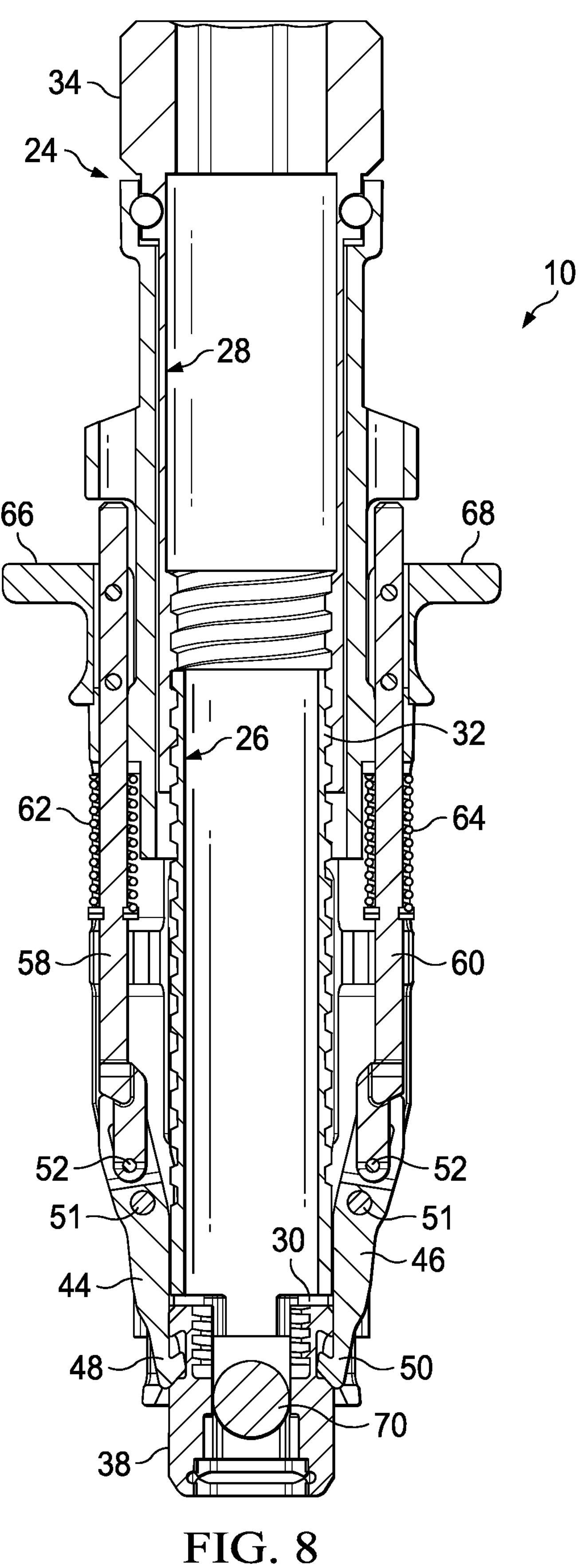
FIG. 8 is a cross-sectional view of the rod reduction device of FIG. 1 in the reduced position.
Figure 9:
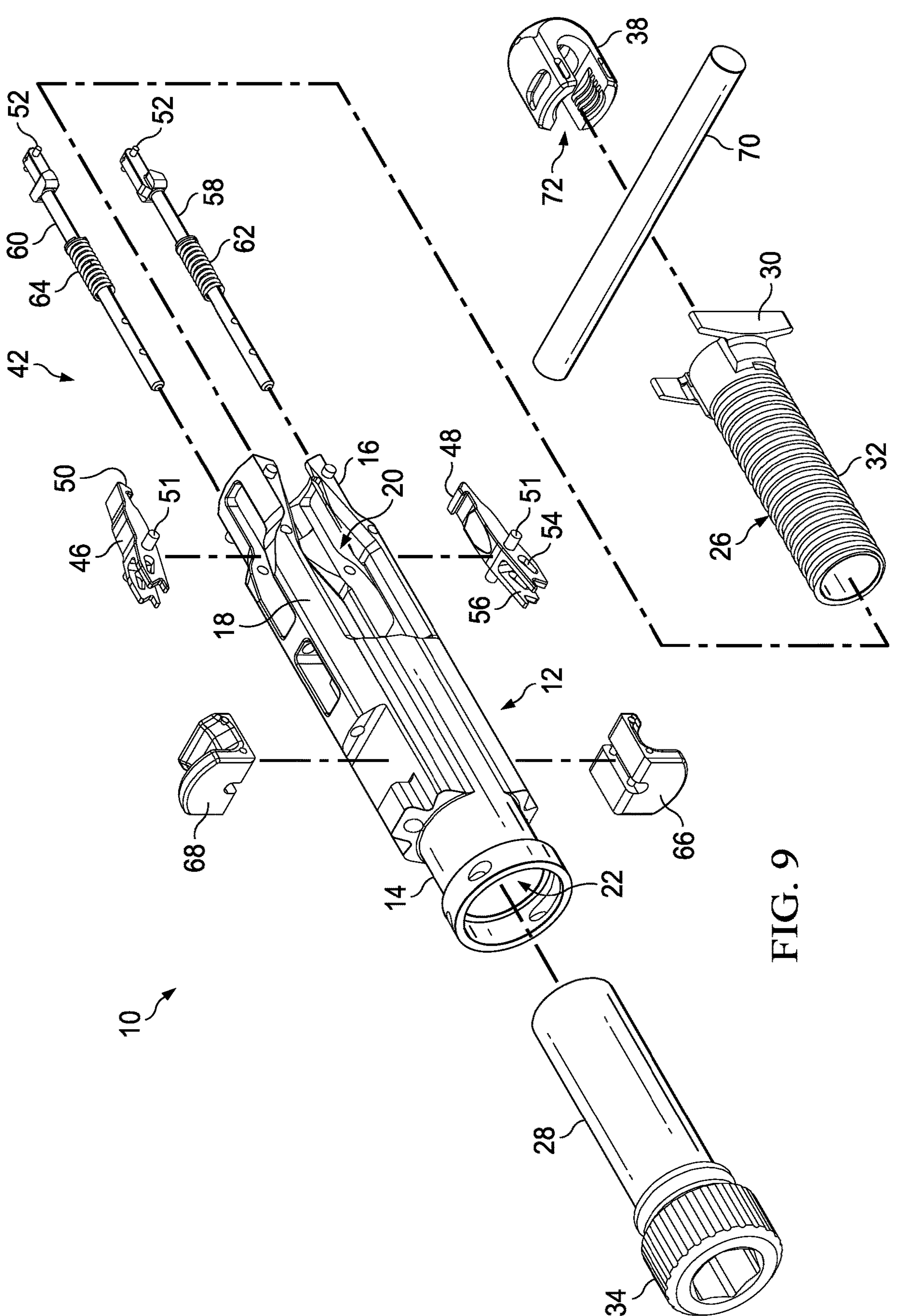
FIG. 9 is a top exploded view of the rod reduction device of FIG. 1.
Figure 10:
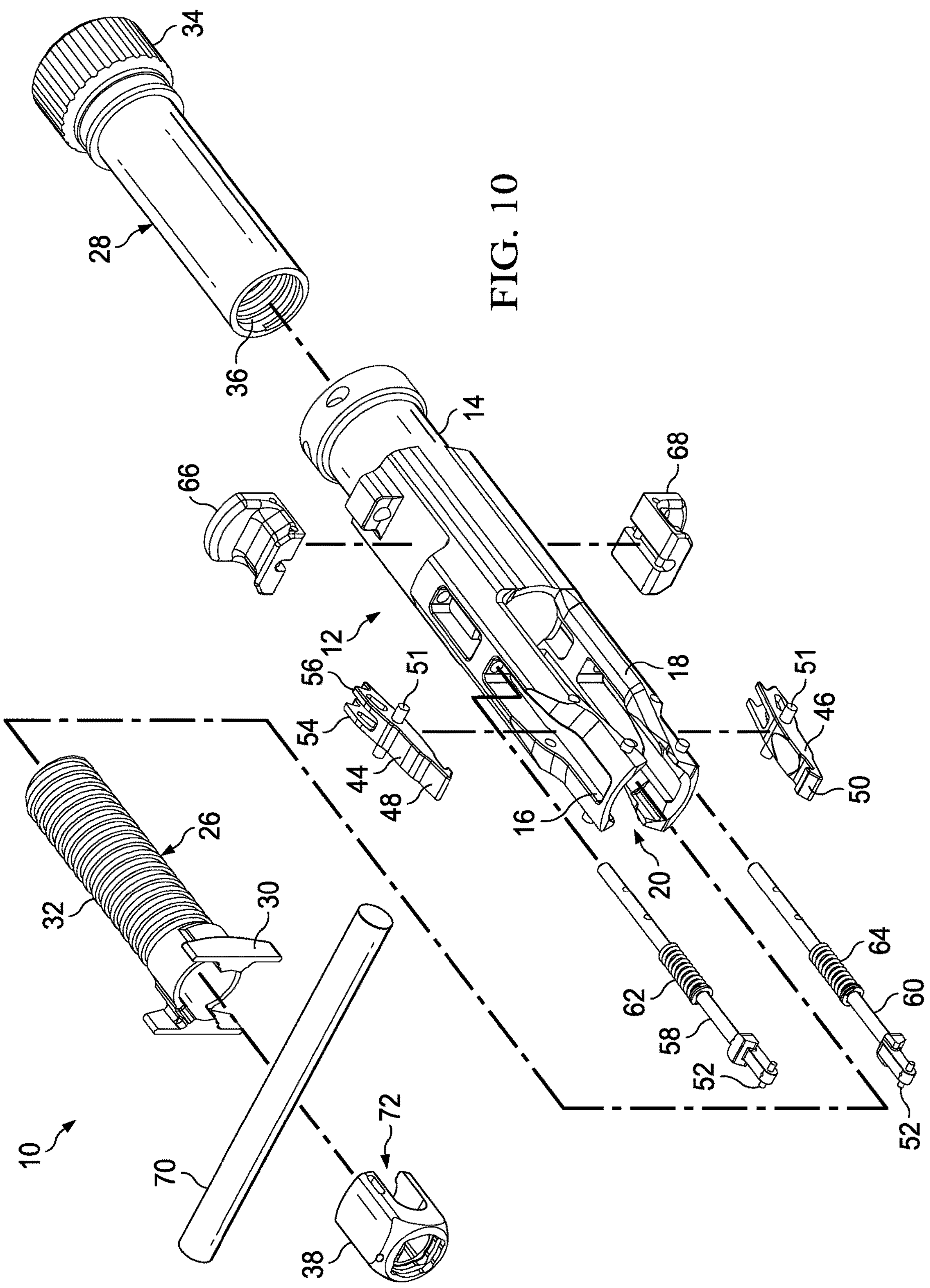
FIG. 10 is a bottom exploded view of the rod reduction device of FIG. 1.

As best shown in FIGS. 4 and 8, the screw assembly 24 can include an inner shaft 26 and an outer shaft 28, where the outer shaft can substantially surround or circumscribe the inner shaft 26. It will be understood that while the inner shaft 26 may be at least partially surrounded or circumscribed by the outer shaft 28 as it moves relative to the outer shaft 28. As illustrated in FIGS. 5, 7, and 8, for example, the inner shaft 26 can include a reduction carriage 30 at a distal end thereof. The reduction carriage 30 may be fixedly or rotatably connected to the distal end of the inner shaft 26. Thus, in certain embodiments, the reduction carriage can be moved rotationally relative to the inner shaft 26. Further, the inner shaft 26 can include exterior threading 32 on at least a portion of an outer surface thereof. The outer shaft 30 can include a knob 34 at a proximal end thereof. The outer shaft 28 can include interior threading 36 on at least a portion of an inner surface thereof. It will be appreciated that the exterior threading 32 of the inner shaft 26 can be threadably engaged with interior threading 36 of the outer shaft 28.

Referring now to FIG. 4, for example, the rod reduction device 10 can be configured to releasably engage a vertebral anchor, such as a bone anchor 38. The first and second members 16, 18 can include a track that can be configured to receive first and second finger assemblies 40, 42. The first and second finger assemblies 40, 42 can include a first and second finger 44, 46, respectively, each of which can include a finger tip 48, 50 at a distal end thereof. Each finger 44, 46 can be configured to engage an outer portion of the bone anchor 38. In certain embodiments, finger tips 48, 50 can facilitate the securement of the first and second fingers 44, 46, and thus the rod reduction device 10, to the bone anchor 38.

Referring to FIG. 4, each finger 44, 46 can be configured to receive a stationary pin 51 and a slidable pin 52. As shown in FIG. 4, for example, each finger 44, 46 can be secured to the first and second members 16, 18, respectively, by the stationary pin 51, such that the finger 44, 46 can be pivotable relative to the member 16, 18 to which it is connected, about an axis defined by the pin 51.

Likewise, a proximal end of each finger 44, 46 can include complementary internal channels 54 on two parallel prongs 56. The internal channels 54 can be configured to receive pin 52, which in operation, can slide between the ends of the respective internal channels 54. The pin 52 can be connected to a distal end of a rod 58. In one embodiment, opposite ends of the pin 52 can be secured by two prongs extending from the distal end of the rod 58. As a result of being connected by the slidable pin 52, each of the first and second fingers 44, 46 can be rotatable relative to the first and second rods 58, 60, respectively, about an axis defined by the pin 52.

As shown in FIG. 4, for example, the respective connections between the first and second fingers 44, 46 and the first and second members 16, 18 at pins 51 can be radially inward of the respective connections between the first and second fingers 44, 46 and the first and second rods 58, 60 at pins 52. Accordingly, in such embodiments, proximal movement of the rods 58, 60 can cause the pins 52 to slide within the internal channels 54 to cause the distal ends of the fingers 44, 46 to rotate or pivot radially outwardly.

A proximal end of each of the first and second rods 58, 60 can be connected to a distal end of a spring 62, 64. The first and second springs 62, 64 can bias the first and second rods in a substantially distal direction, respectively. Further, as result of such bias, the finger tips 48, 50 are biased radially inwardly. In certain embodiments, a proximal end of each spring 62, 64 can be connected to a lever 66, 68. Each of the first and second levers 66, 68 can be configured to slide within the finger assembly track.

In operation, a rod reduction device 10 may be positioned over and slid onto a bone anchor 38. For example, as distal ends of the fingers 44, 46 are biased radially inwardly, the bone anchor 38 can slide therebetween, urging the distal ends of the fingers 44, 46 radially outwardly before the finger tips 48, 50 snap into pockets on opposite sides of the bone anchor 38 to engage the same, thereby attaching the rod reduction device 10 to the bone anchor 38.

In operation, when a user urges the first and second levers 66, 68 in a proximal direction, each of the first and second rods 58, 60 is drawn back by the springs 62, 64, thereby pulling the pins 52 substantially proximally within the internal channels 54. As a result of such movement, the fingers 44, 46, secured to the members 16, 18 by stationary pins 51, are forced to rotate or pivot about such pins 51, causing the finger tips 48, 50 at distal ends of the fingers 44, 46 to move outwardly. Accordingly, such proximal movement of the levers 66, 68 may allow the bone anchor 38 to be released from the securement of the fingers 44, 46. Similarly, when the levers 66, 68 are released, the springs 62, 64 can bias the rods 58, 60 in a distal position, thereby forcing the distal ends of the fingers 44, 46 (e.g., finger tips 48, 50) radially inwardly. Similar mechanisms for attaching a rod reduction device 10 to bone anchor 38 are described in U.S. Pat. Nos. 9,844,398 and 10,729,472, which are incorporated herein by reference.

Upon attachment of the rod reduction device 10 to the bone anchor 38, a spinal rod 70 may be guided into the channel 20, between the first and second members 16, 18, to be reduced into the bone anchor 38. The rod reduction device 10 can move between a retracted position, as shown, for example, in FIGS. 1-4, and a reduced position, as shown, for example, in FIGS. 5-8. In operation, the knob 34 of the outer shaft 28 can be rotated to effect linear, distal movement of the inner shaft 26 and reduction carriage 30, from the retracted position to the reduced position, such that the reduction carriage 30 will engage the spinal rod 70 and urge the spinal rod 70 into a slot 72 of the bone anchor 38. When the outer shaft 28 is rotated, it does not move upwardly or downwardly relative to the body 12 of the rod reduction device 10. That is, the outer shaft 28 may be coupled, attached, or connected to the body 12, such that the outer shaft 28 can rotate relative to the body 12 while being longitudinally fixed to the body 12, i.e., stationary or fixed along the longitudinal axis. Rather, the reduction carriage 30 of the inner shaft 26 can move upwardly and downwardly in response to rotation of the knob 34 of the outer shaft 28.

Referring to FIG. 1, for example, the knob 34 of the outer shaft 28 can be an actuating rotational member, rotatably coupled to the body 12. Thus, the knob 34 and outer shaft 28 can rotate relative to the body 12. The outer shaft 28 can be cannulated, and as described above, have interior threading 36. The inner shaft 26, also a cannulated component, can have exterior threading 32 that can engage with the interior threading 36 of the outer shaft 28. The inner shaft 26 can translate along the longitudinal axis of the screw assembly 24 in response to rotation of the knob 34 of the outer shaft 28.

Thus, in operation, the rod reduction device 10 can display a turn-buckle style actuation mechanism. With the spinal rod 70 positioned in the channel 20, as described above, the rod reduction device 10 can be ready to begin reducing the spinal rod 70 into the bone anchor 38. Rotating the knob 34, which can be rotatably coupled to the proximal end of the housing 14, can cause the inner shaft 26, and thus the reduction carriage 30, to translate distally into contact with the spinal rod 70. Continued turning of the knob 34 can effect translation of the reduction carriage 30 to ultimately drive the spinal rod 70 into the slot 72 of the bone anchor 38, as best shown in FIGS. 5-8. Turning of the knob 34 in the reverse direction can cause the inner shaft to translate proximally.

Components of the rod reduction device may be formed of any of a variety of suitable materials. In certain embodiments, the components may be formed from one or more of titanium alloy, in accordance with American Society for Testing and Materials (ASTM) F-136; commercially pure titanium, in accordance with ASTM F-67; and cobalt-chromium-molybdenum alloy, in accordance with ASTM F-1537.

The above relates to an exemplary surgical technique and other known and accepted methods or techniques for performing steps outlined within the technique may be substituted where appropriate. In certain embodiments, the rod reducing device may be used for immobilization and stabilization of the posterior, non-cervical spine in skeletally mature patients as an adjunct to fusion for one or more of the following: degenerative disc disease, spondylolisthesis, trauma, spinal stenosis, curvatures, tumor, pseudarthrosis, and failed previous fusion.

The previous text sets forth a broad description of numerous different embodiments. The description is to be construed as exemplary only and does not describe every possible embodiment since describing every possible embodiment would be impractical, if not impossible, and it will be understood that any feature, characteristic, component, step or methodology described herein can be deleted, combined with or substituted for, in whole or part, any other feature, characteristic, component, step or methodology described herein. Numerous alternative embodiments could be implemented, using either current technology or technology developed after the filing date of this patent, which would still fall within the scope of the claims.

It should also be understood that, unless a term is expressly defined in this specification using the sentence "As used herein, the term '______' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph or similar doctrine.

It is also noted that recitations herein of "at least one" component, element, etc., should not be used to create an inference that the alternative use of the articles "a" or "an" should be limited to a single component, element, etc.

It is noted that recitations herein of a component of the present disclosure being "configured" to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Rather, the claims appended hereto should be taken as the sole representation of the breadth of the present disclosure and the corresponding scope of the various inventions described herein. Further, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these aspects.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made. It is therefore intended to cover in the appended claims all such changes and modifications.

What is claimed is:

1. A rod reduction device comprising:

a body including a housing defining a cavity;

a first member and a second member, each of the first and second members extending distally from the housing;

a first finger assembly and a second finger assembly being secured to respective distal ends of the first member and the second member, wherein the first finger assembly and the second finger assembly are configured to, collectively, releasably engage a vertebral anchor therebetween, wherein the first and second finger assemblies comprise a first finger and a second finger, respectively, each of the first and second fingers having a finger tip at a distal end thereof, and wherein each of the first and second fingers is pivotable relative to its respective member; and a screw assembly defining a longitudinal axis, at least a portion of the screw assembly being positioned within the cavity of the housing, wherein the screw assembly comprises:

an inner shaft having exterior threading; and an outer shaft having interior threading and circumscribing the inner shaft, wherein at least a portion of the outer shaft is rotatably coupled to the housing, wherein the exterior threading of the inner shaft is threadably engaged with the interior threading of the outer shaft, and wherein the inner shaft is movable along the longitudinal axis upon rotation of the outer shaft and configured to reduce a spinal rod into the vertebral anchor.

2. The rod reduction device of claim 1, further comprising a reduction carriage connected to a distal end of the inner shaft.

3. The rod reduction device of claim 2, wherein the reduction carriage is fixedly connected to the distal end of the inner shaft.

4. The rod reduction device of claim 2, wherein the reduction carriage is rotationally connected to the distal end of the inner shaft.

5. The rod reduction device of claim 2, wherein the reduction carriage is configured to urge a spinal rod into the vertebral anchor.

6. The rod reduction device of claim 2, wherein the reduction carriage is movable between a retracted position and a reduced position.

7. The rod reduction device of claim 1, wherein the outer shaft further comprises a knob, wherein the knob is fixedly connected to a proximal end of the outer shaft.

8. The rod reduction device of claim 1, wherein the outer shaft is not translatable relative to the housing along the longitudinal axis.

9. The rod reduction device of claim 1, wherein the first member and the second member collectively define a channel configured to receive a spinal rod.

10. The rod reduction device of claim 1, wherein the finger tip of each of the first and second fingers is configured to engage opposite sides of the vertebral anchor.

11. The rod reduction device of claim 10, wherein the finger tip of each of the first and second fingers is configured to snap into pockets on the opposite sides of the vertebral anchor.

12. The rod reduction device of claim 1, further comprising a first rod and a second rod, wherein distal ends of the first and second rods are movably secured to proximal ends of the first and second fingers, respectively, such that the first and second fingers are rotatable relative to the first and second rods, respectively.

13. The rod reduction device of claim 12, further comprising a first lever and a second lever, wherein the first and second levers are slidable within tracks on the first and second members, respectively, and connected to the first and second rods, respectively, by respective first and second springs.

14. The rod reduction device of claim 13, wherein the first and second fingers are biased radially inwardly.

15. The rod reduction device of claim 13, wherein proximal movement of the levers causes outward rotation of the first and second fingers.

* * * * *